(12) United States Patent
Brown

(10) Patent No.: US 9,204,930 B2
(45) Date of Patent: Dec. 8, 2015

(54) THERMAL INDUCED NECROSIS OF LENS EPITHELIAL CELLS

(71) Applicant: David C. Brown, Fort Myers, FL (US)

(72) Inventor: David C. Brown, Fort Myers, FL (US)

(*) Notice: Subject to any disclaimer, the term of this patent is extended or adjusted under 35 U.S.C. 154(b) by 0 days.

(21) Appl. No.: 14/080,022

(22) Filed: Nov. 14, 2013

(65) Prior Publication Data

US 2014/0148800 A1 May 29, 2014

Related U.S. Application Data

(60) Provisional application No. 61/731,342, filed on Nov. 29, 2012.

(51) Int. Cl.
| | |
|---|---|
| *A61B 18/18* | (2006.01) |
| *A61F 9/007* | (2006.01) |
| *A61F 9/00* | (2006.01) |
| *A61B 18/00* | (2006.01) |
| *A61B 18/04* | (2006.01) |
| *A61B 18/14* | (2006.01) |
| *A61F 9/008* | (2006.01) |

(52) U.S. Cl.
CPC ........... *A61B 18/1815* (2013.01); *A61F 9/0079* (2013.01); *A61B 2018/00321* (2013.01); *A61B 2018/046* (2013.01); *A61B 2018/144* (2013.01); *A61B 2018/1407* (2013.01); *A61F 9/0017* (2013.01); *A61F 2009/0087* (2013.01)

(58) Field of Classification Search
CPC ...... A61N 7/02; A61B 18/08; A61B 18/1815; A61B 2018/00321; A61B 2018/044; A61B 2018/046; A61B 2018/048; A61B 2018/082; A61B 2018/1407; A61B 2018/144; A61F 9/0017; A61F 9/0079; A61F 2009/0087
USPC .............................................. 606/27; 600/383
See application file for complete search history.

(56) References Cited

U.S. PATENT DOCUMENTS

| | | | | |
|---|---|---|---|---|
| 5,489,299 | A | * | 2/1996 | Schachar ...................... 623/4.1 |
| 6,006,756 | A | * | 12/1999 | Shadduck ..................... 128/899 |
| 6,887,261 | B1 | * | 5/2005 | Peyman ......................... 607/89 |
| 7,806,929 | B2 | * | 10/2010 | Brown ......................... 623/6.39 |
| 8,591,577 | B2 | * | 11/2013 | Moradian et al. .............. 623/4.1 |
| 2008/0177383 | A1 | * | 7/2008 | Shahinpoor et al. ......... 623/5.12 |
| 2011/0282335 | A1 | * | 11/2011 | Jia et al. ......................... 606/27 |
| 2011/0295367 | A1 | * | 12/2011 | Cuevas ........................ 623/6.43 |
| 2013/0304206 | A1 | * | 11/2013 | Pallikaris et al. ............ 623/6.43 |

* cited by examiner

*Primary Examiner* — Jaymi Della
(74) *Attorney, Agent, or Firm* — Tumey L.L.P.

(57) ABSTRACT

Lens epithelial cells are destroyed and further growth is inhibited coincidental with eye surgery such as cataract surgery by heating the cells to a temperature above normal to thereby destroy the cells and inhibit future growth. The cells are heated by placement of a thermally conductive ring within the lens capsule and heating the ring thereby raising the temperature of lens epithelial cells adjacent to the ring.

10 Claims, 1 Drawing Sheet

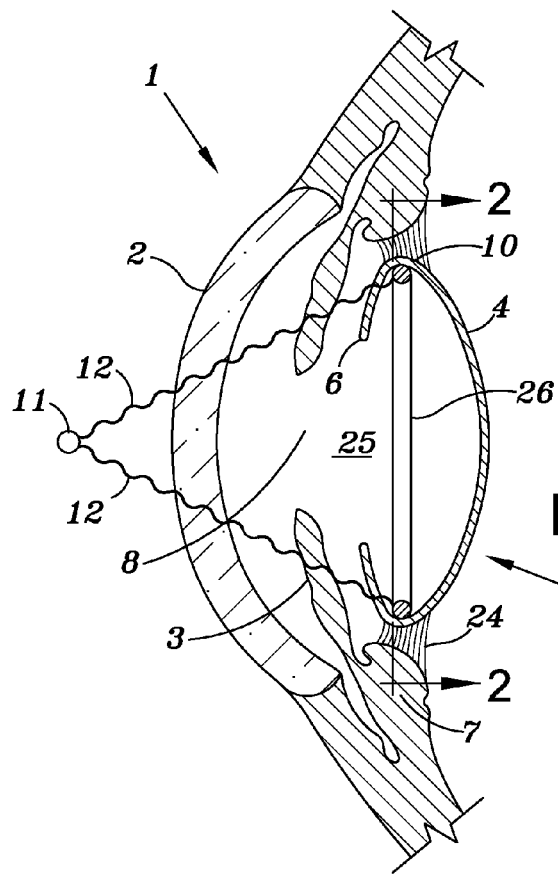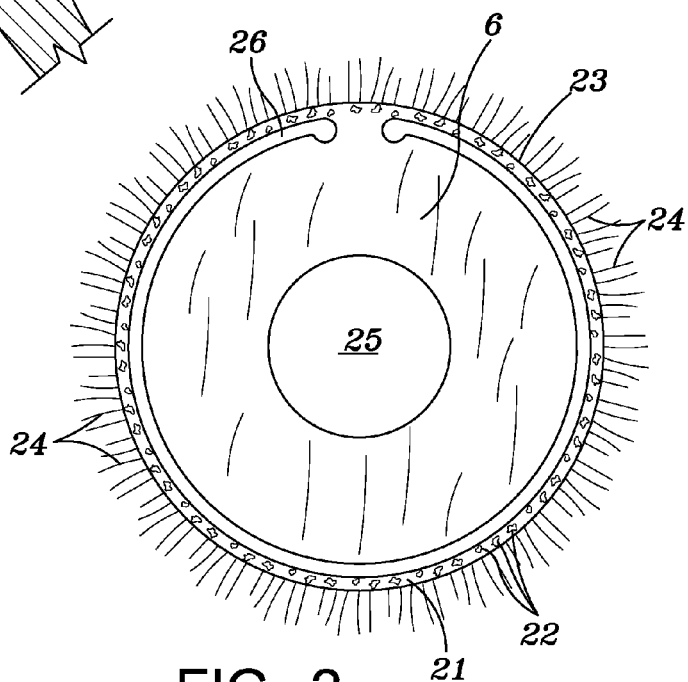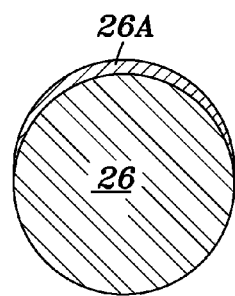

THERMAL INDUCED NECROSIS OF LENS EPITHELIAL CELLS

This application claims priority to U.S. provisional application Ser. No. 61/731,342 filed on Nov. 29, 2012.

BACKGROUND OF INVENTION

1. Field of the Invention

This invention relates to eye treatment procedures and devices and particularly to a technique for destroying lens epithelial cells that remain after portions of the natural lens (cataract) has been removed from an eye. Epithelial cells remaining after the natural lens has been removed need to be eliminated to the maximum extent possible, to prevent formation of secondary cataracts. This invention relates to a novel technique for inducing necrosis of the epithelial cells in the lens capsule and to a specially designed ring implant for use with the method is disclosed herein.

2. Description of Related Art

Currently during cataract surgery, a conventional phacoemulsification instrument is used to apply ultrasonic energy to the lens, which breaks up or emulsifies the cataract. An aspiration passageway carries away the fragmented portions of the cataract and an irrigation passageway provides an irrigating fluid to the interior of the lens capsule to clear out the fragments. This procedure is commonly called "irrigation and aspiration". In addition to removing the lens it is desirable to remove epithelial cells remaining in the lens capsule prior to insertion of the replacement lens, which remain after irrigation and aspiration.

Currently there are several proposed approaches to destroying or mitigating the growth of epithelial cells after cataract surgery and prior to insertion of a replacement lens. They include the use of chemical compounds injected into the lens capsule to kill the cells, the insertion of a capsular tension ring having an inhibitor compound on its surface or various designs to provide a physical barrier to inhibit proliferation and migration of the lens epithelial cells in the posterior capsule of the eye.

BRIEF SUMMARY OF THE INVENTION

The invention disclosed is directed to a method of destroying lens epithelial cells by implanting a biocompatible annular ring into the lens capsule after removing the natural lens and heating the ring to a temperature sufficient to destroy the lens epithelial cells but not sufficient to destroy the surrounding tissue of the eye. The ring may be removed or retained in the eye as an additional barrier to cell migration and to support the capsule.

BRIEF DESCRIPTION OF THE SEVERAL VIEWS OF THE DRAWING(S)

FIG. 1 is a schematic view of the eye in cross-section after the natural lens has been removed and the ring implanted.

FIG. 2 is a frontal view of the lens capsule shown in FIG. 1.

FIG. 3 is a cross-sectional view of the tension ring with a partial coating of an insulating or heat absorbing material.

DETAILED DESCRIPTION OF THE INVENTION

FIG. 1 illustrates the main parts of the human eye 1 including cornea 2, iris 3, pupil 8, ciliary muscle 7, zonules 24 and lens capsule 9 having an anterior wall portion 6 and a posterior wall portion 4. The anterior and posterior wall portions of the lens capsule come together and form an annular groove 10 in which lens epithelial cells 22 shown in FIG. 2 tend to concentrate.

An opening or capsolotomy 25 is typically formed in the anterior portion of the lens capsule. According to the invention, an annular ring member 26 shown in FIGS. 1 and 2 is surgically implanted after removal of the lens. Conventional techniques may be used to implant the ring. The ring may be formed of an inert, biocompatible material that is capable of transferring heat to the cells located in the groove portion 10 of the lens capsule.

In one embodiment, an external microwave source 11 emitting microwaves 12 may serve as the heat source for generating heat in the ring 26. In this instance, ring 26 would be formed of a material that absorbs microwaves and converts the microwave energy to heat energy. Any known method of heating ring 26 may be used such as electrical resistance of the ring or the use of an electromagnetic field in the vicinity of ring 26.

The ring may be a capsular tension ring, which may be made electrically or thermally conductive. The ring may have various sizes and shapes and an injector may be utilized for inserting the ring into the lens capsule. Alternatively, the ring is to be composed of metallic or biocompatible thermally conductive material.

The ring may be hollow so that a warm saline fluid or other liquid could be circulated through it to transfer the heat to the cells via a temperature controlled external source.

In one embodiment, the energy level of the microwave source and the material chosen for the ring should result in a cell temperature between about 42° C. and 60° C. as research has demonstrated that cells begin to die at 42° C. and temperatures at about 60° C. or higher cause denaturation to occur, which immediately kills the cell. See for example, the discussion of temperature and cell behavior in U.S. Pat. No. 6,887,261 B1 the entire contents of which is hereby expressly incorporated herein.

In the embodiment shown in FIG. 3, tension ring 26 is partially coated with an insulating or heat absorbing material such as a matrix containing phase change material. The coating is placed on the portion of the ring that comes into contact with the lens capsule which would be at the juncture of the anterior and posterior walls of the capsule generally indicated at 10 in FIG. 1. This would protect the lens capsule tissue zonules from being overheated and possibly damaged as a result of excessive heat.

The anterior chamber or lens capsule may be irrigated with lower temperature fluid to minimize or control damage to the zonules due to excessive heating.

Although the present invention has been described with respect to specific details, it is not intended that such details should be regarded as limitations on the scope of the invention, except to the extent that they are included in the accompanying claims.

I claim:

1. A method of destroying and inhibiting the growth of lens epithelial cells within a lens capsule of an eye during or after an eye surgical procedure comprising:
    implanting a ring made from an inert biocompatible material into the lens capsule, the ring being capable of transferring heat to an interior portion of the lens capsule; and heating the ring within the lens capsule so as to raise a temperature of epithelial cells located within the lens capsule to a level where the epithelial cells begin to die.

2. The method of claim 1 wherein the ring is heated by exposure to microwaves from a source positioned outside of the eye.

3. The method of claim 1 wherein the ring is heated by electrical resistance.

4. The method of claim 1 wherein the ring is heated an electromagnetic field.

5. The method of claim 1 wherein the ring is hollow.

6. The method of claim 5 wherein the ring is heated by a fluid flowing within the ring.

7. The method of claim 1 wherein the ring is a capsular tension ring.

8. The method of claim 1 wherein the ring has a coating of an insulating or heat absorbing material on an outer surface of the ring.

9. The method of claim 1 further including the step of irrigating the lens capsule with a fluid having a lower temperature than a temperature of the ring while heating the ring.

10. The method of claim 1 wherein the ring is implanted in an annular groove formed at a juncture of anterior and posterior walls of the lens capsule.

* * * * *